(12) United States Patent
Al-Ali

(10) Patent No.: US 6,697,656 B1
(45) Date of Patent: Feb. 24, 2004

(54) PULSE OXIMETRY SENSOR COMPATIBLE WITH MULTIPLE PULSE OXIMETRY SYSTEMS

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/604,340

(22) Filed: Jun. 27, 2000

(51) Int. Cl.⁷ .................................................. A61B 5/00
(52) U.S. Cl. ........................ 600/323; 600/310; 439/909
(58) Field of Search ................................ 600/309–310, 600/322–324; 356/39–42; 439/909

(56) References Cited

U.S. PATENT DOCUMENTS

| | | | |
|---|---|---|---|
| 4,684,245 A | 8/1987 | Goldring | |
| 5,249,576 A | * 10/1993 | Goldberger et al. | 600/323 |
| 5,287,853 A | 2/1994 | Vester et al. | |
| 5,387,122 A | 2/1995 | Goldberger et al. | |
| 5,632,272 A | 5/1997 | Diab et al. | |
| 5,758,644 A | 6/1998 | Diab et al. | |
| 5,769,785 A | 6/1998 | Diab et al. | |
| 5,782,757 A | 7/1998 | Diab et al. | |
| 5,807,247 A | * 9/1998 | Merchant et al. | 600/310 |
| 5,818,985 A | * 10/1998 | Merchant et al. | 385/20 |
| 5,830,137 A | * 11/1998 | Scharf | 600/323 |
| 5,995,855 A | * 11/1999 | Kiani et al. | 600/310 |
| 5,995,858 A | * 11/1999 | Kinast | 600/323 |
| 6,002,952 A | 12/1999 | Diab et al. | |
| 6,061,584 A | * 5/2000 | Lovejoy et al. | 600/344 |
| 6,349,228 B1 | 2/2002 | Kiani et al. | |

FOREIGN PATENT DOCUMENTS

EP 0 538 631 A1 9/1992 ............ A61B/5/00

OTHER PUBLICATIONS

Copy of October 4, 2001 Communication from European Paten Office with copy of European Search Report.

* cited by examiner

Primary Examiner—Eric F. Winakur
Assistant Examiner—Matthew J Kremer
(74) Attorney, Agent, or Firm—Knobbe, Martens Olson & Bear LLP.

(57) ABSTRACT

An oximeter sensor can be used with multiple oximeter systems. The oximeter sensor includes a first light-emitting diode, a second light-emitting diode and a photodetector. Electrical connections to the anode and the cathode of each light-emitting diode and electrical connections to the terminals of the photodetector are provided on a connector. An interconnector is interposed between the connector of the oximeter sensor and a connector in communication with an oximeter system. The interconnector has interconnection wiring selected to electrically connect the sensor connector and the system connector in a manner to configure the light-emitting diodes in a configuration compatible with the oximeter system. In particular, a first interconnector configures the light-emitting diodes in a common anode arrangement. A second interconnector configures the light-emitting diodes in a back-to-back (anode to cathode, cathode to anode) configuration. Either interconnector may be in the form of a shell having two connectors. Alternatively, either interconnector may be in the form of a flexible cable with connectors at each end.

12 Claims, 9 Drawing Sheets

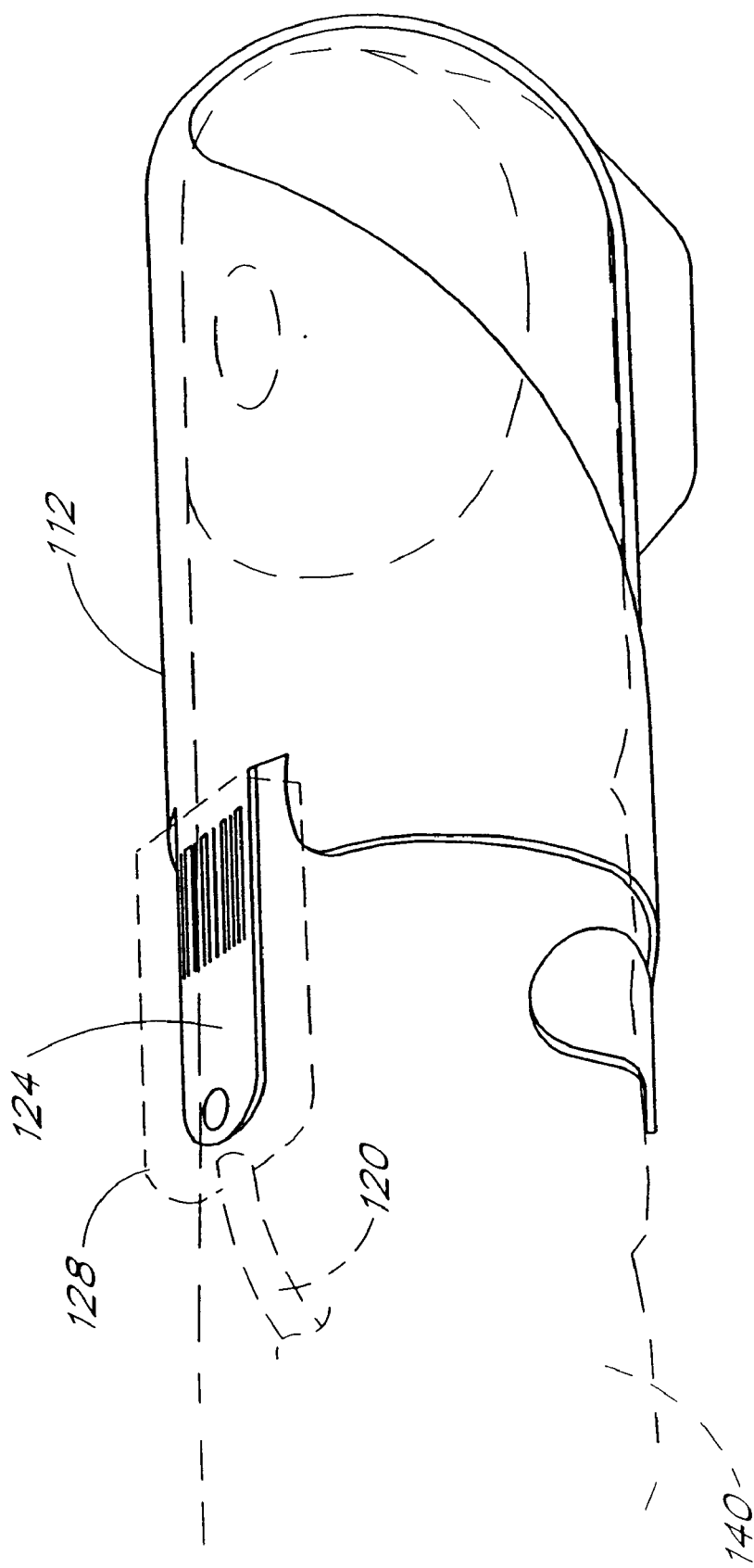

PULSE OXIMETRY SENSOR COMPATIBLE WITH MULTIPLE PULSE OXIMETRY SYSTEMS

BACKGROUND OF THE INVENTION

1. Field of the Invention

The present invention is directed to the field of pulse oximetry sensing, and, more particularly, is directed to a sensor for use with pulse oximetry sensing systems.

2. Description of the Related Art

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed oximetry, a study and measurement of the oxygen status of blood. One particular type of oximetry, pulse oximetry, is a widely accepted noninvasive procedure for measuring the oxygen saturation level of arterial blood, an indicator of the oxygen status of the blood. A pulse oximeter relies on a sensor attached to a patient in order to measure the blood oxygen saturation.

Conventionally, a pulse oximeter sensor has a red emitter, an infrared emitter, and a photodiode detector. The sensor is typically attached to a patient's finger, earlobe, or foot. For a finger, the sensor is configured so that the emitters project light through the outer tissue of the finger and into the blood vessels and capillaries contained inside. The photodiode is positioned at the opposite side of the finger to detect the emitted light as it emerges from the outer tissues of the finger. The photodiode generates a signal based on the emitted light and relays that signal to an oximeter. The oximeter determines blood oxygen saturation by computing the differential absorption by the arterial blood of the two wavelengths (red and infrared) emitted by the sensor.

There are at least two general types of sensor devices in use in the pulse oximetry industry. A first type has the red emitter and the infrared emitter connected in back-to-back configuration. That is, the red emitter and the infrared emitters are light-emitting diodes, each of which has a respective anode and a respective cathode. As is well-known in the art, when a sufficient voltage of the proper polarity is applied across the anode and cathode of a light-emitting diode, the light-emitting diode will emit light of a predetermined wavelength (e.g., red light or infrared light). By connecting the light-emitting diodes in a back-to-back configuration, the same voltage source can be applied to both light-emitting diodes. Thus, when the voltage source has a first polarity, one of the two light-emitting diodes is activated to emit light, and when the voltage source has the opposite polarity, the other light-emitting diode is activated to emit light. It can be understood that only two connections are needed from the oximeter system to the light-emitting diodes. (See, for example, U.S. Pat. No. 5,758,644, assigned to the assignee of the present application, and incorporated by reference herein. See, in particular, FIG. 8A of U.S. Pat. No. 5,758,644.) The photodetector can be advantageously connected between one of the two connections and third connection so that both the light-emitting diodes and the photodetector are connected to the oximeter system by only three interconnection wires.

The second type of sensor in general use connects the two emitters in a common electrode configuration. That is, one of the two electrodes of each emitter (e.g., the cathode of each emitter) is connected in common to one connection to the oximeter system. The other electrode (e.g., the anode) of each emitter has a separate connection to the oximeter system, thus requiring a total of three connections for the emitters. The photodetector has at least one extra connection to the oximeter system, thus requiring a total of four connectors for the sensor. (See, for example, FIG. 4A of U.S. Pat. No. 5,578,644.)

Because oximeter systems are generally designed to be used with one of the two sensors described above, its is necessary for a hospital having both types of oximeter systems to stock a supply of three-wire sensors to be compatible with oximeter systems designed for back-to-back emitters and to stock a supply of four-wire sensors to be compatible with oximeter systems designed for common electrode sensors. Although conversion units are commercially available to permit three-wire sensors to be used with four-wire oximeter systems and other conversion units are commercially available to permit four-wire sensors to be used with three-wire oximeter systems, such conversion units are expensive and typically include conversion electronics that must be powered from a separate power supply. Because the conversion units and the required electrical connections for the conversion units are bulky by nature, the conversion units are particularly unattractive in a hospital setting, such as a surgical room.

SUMMARY OF THE INVENTION

One aspect of the present invention is an oximeter sensor for use with multiple oximeter systems. The oximeter sensor comprises a first light-emitting diode having an anode and a cathode. The first light-emitting diode emits light of a first wavelength when a sufficient voltage is applied from the anode to the cathode. The sensor further comprises a second light-emitting diode having an anode and a cathode. The second light-emitting diode emits light of a second wavelength when a sufficient voltage is applied from the anode to the cathode. The sensor comprises a photodetector having a first terminal and a second terminal. The photodetector has a measurable characteristic that responds to varying intensities of light incident on the photodetector. The sensor comprises a sensor connector having a first contact coupled to the anode of the first light-emitting diode, a second contact coupled to the cathode of the first light-emitting diode, a third contact coupled to the anode of the second light-emitting diode, a fourth contact coupled to the cathode of the second light-emitting diode, a fifth contact coupled to the first terminal of the photodetector and a sixth contact coupled to the second terminal of the photodetector. In accordance with this aspect of the invention, the oximeter sensor further comprises an interconnector for interconnecting the oximeter sensor with an oximeter system monitor. The interconnector includes a first connector having contacts engageable with the contacts of the sensor connector. The interconnector includes a second connector having contacts engageable with contacts in a connector on the oximeter system monitor. The interconnector electrically connects selected contacts of the first connector to selected contacts of the second connector to electrically interconnect the first light-emitting diode, the second light-emitting diode and the photodetector to the oximeter system monitor. In one embodiment, the interconnector comprises a shell having the first connector on a first end and having the second connector on a second end. In an alternative embodiment, the interconnector comprises a flexible cable having the first connector at a first end and having the second connector on a second end. In one application for use with a five-wire oximeter monitoring system, the interconnector electrically interconnects the first light-emitting diode and the second light-emitting diode in a common anode configuration. In an alternative application for use with a four-wire oximeter monitoring system, the interconnector electrically interconnects the first light-emitting diode and the second light-emitting diode in a back-to-back configuration wherein the anode of the first light-emitting diode is connected to the cathode of the second light-emitting diode and wherein the cathode of the first light-emitting diode is connected to the anode of the second light-emitting diode.

Another aspect of the present invention is an interconnector for interconnecting an oximeter sensor to an oximeter system monitor wherein the oximeter sensor has a sensor connector having contacts electrically connected to the anodes and cathodes of first and second light-emitting diodes and having contacts electrically connected to the terminals of a photodetector. The interconnector comprises a first connector having contacts engageable with the contacts of the sensor connector. The interconnector comprises a second connector having contacts engageable with contacts in a system connector in electrical communication with the oximeter system monitor. The interconnector further comprises electrical interconnections between the first connector and the second connector that electrically connect selected contacts of the first connector to selected contacts of the second connector to electrically interconnect the first light-emitting diode, the second light-emitting diode and the photodetector in a configuration compatible with the oximeter system monitor.

BRIEF DESCRIPTION OF THE DRAWINGS

Preferred embodiments of the present invention are described below in connection with the attached drawing figures in which:

FIG. 1A is a pictorial illustration of the oximeter sensor of FIG. 1 mounted on a finger of an patient;

DETAILED DESCRIPTION OF THE PREFERRED EMBODIMENTS

Figure 1:
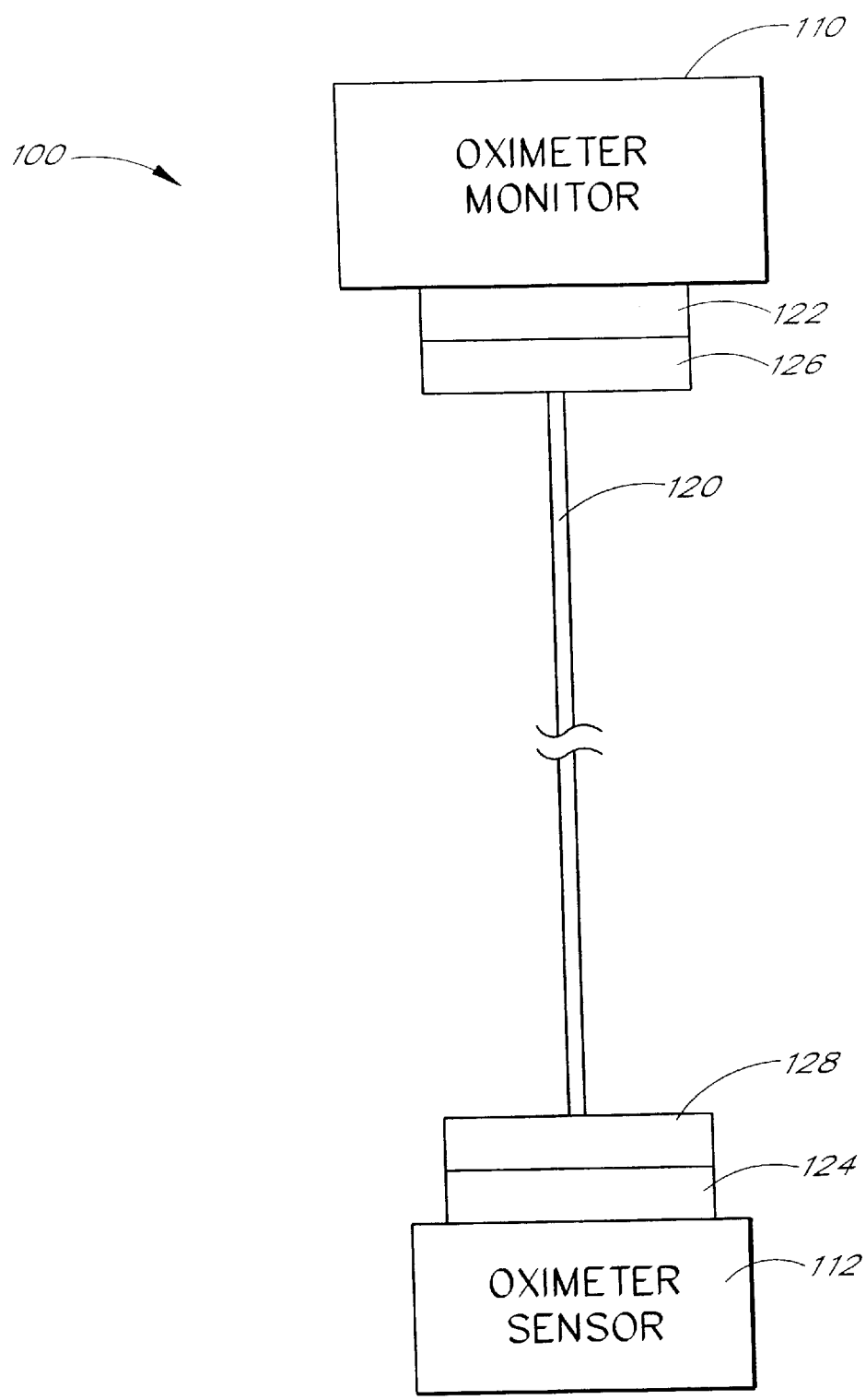
FIG. 1 illustrates a block diagram of an exemplary oximetry system that includes an oximeter monitor and an oximeter sensor.

FIG. 1 illustrates an exemplary oximetry system 100 that includes an oximeter monitor 110 and an oximeter sensor 112. The oximeter monitor 110 and the oximeter sensor 112 are interconnected by an oximeter cable 120. Typically, the oximeter monitor 110 has a connector 122, and the oximeter sensor 112 has a connector 124. In addition, the oximeter cable 120 has a first connector 126 compatible with the oximeter monitor connector 122 and has a second connector 128 compatible with the oximeter sensor connector 124. In operation, the connector 122 and the connector 126 are engaged, and the connector 124 and the connector 128 are engaged to provide electrical connections between the oximeter monitor 110 and the oximeter sensor 112. As is well-known in the art, the oximeter sensor 112 is mounted onto a portion of the patient's body (e.g., mounted onto a patient's finger or a patient's toe) so that the blood oxygenation of the patient can be monitored. See, for example, FIG. 1A, which shows the sensor 112 mounted on an exemplary finger 140 of a patient.

Details regarding the operation of the oximeter sensor and oximeter monitor can be found, for example, in U.S. Pat. Nos. 5,632,272, 5,758,644, 5,769,785, 5,782,757 and 6,002, 952, which are assigned to the assignee of the present application, and which are incorporated by reference herein.

Figure 2:
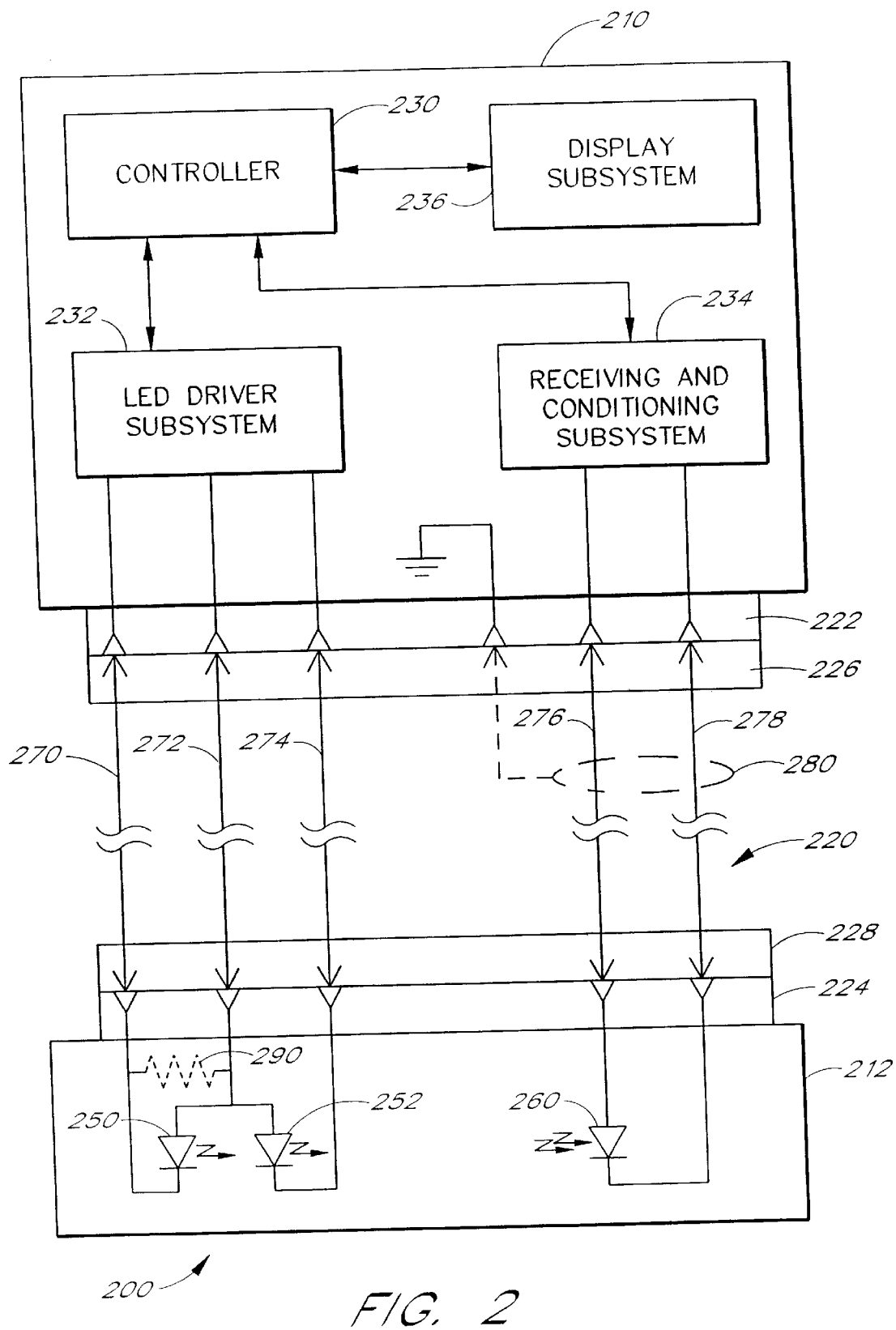
FIG. 2 illustrates a schematic block diagram of an oximeter system which implements the oximeter system of FIG. 1 with light-emitting diodes connected in a common anode configuration.

FIG. 2 illustrates a schematic block diagram of an oximeter system 200 which is an embodiment of the oximeter system 100 of FIG. 1 with a five-wire interconnection for driving a common anode light-emitting diode configuration. In particular, the embodiment of FIG. 2 includes an oximeter monitor 210 and an oximeter sensor 212 that are interconnected by a five-wire cable 220 via a monitor connector 222 and a sensor connector 224. The five-wire cable 220 includes a first connector 226 connected to the monitor connector 222 and a second connector 228 connected to the sensor connector 224.

As illustrated, the oximeter monitor 210 includes a controller 230 that controls a light-emitting diode (LED) driver subsystem 232, that receives information from a receiving and conditioning subsystem 234, and that displays information regarding the patient (e.g., pulse rate and blood oxygenation levels) on a display subsystem 236. The oximeter monitor 210 may include other subsystems (not shown), such as, for example, a power supply subsystem, a user interface, and the like.

The oximeter sensor 212 includes a first light-emitting diode 250 having an anode and a cathode. The first light-emitting diode 250 advantageously emits light of a first wavelength (e.g., light in the red portion of the electromagnetic spectrum), when a sufficiently high voltage is applied from the anode to the cathode.

The oximeter sensor 212 includes a second light-emitting diode 252 having an anode and a cathode. The second light-emitting diode 252 advantageously emits light of a second wavelength (e.g., light in the infrared portion of the electromagnetic spectrum), when a sufficiently high voltage is applied from the anode to the cathode.

The oximeter sensor 212 includes a photodetector (e.g., a photodiode) 260, which has an anode and a cathode. The photodetector 260 operates in a known manner to vary the conduction of an electrical current from the anode to the cathode when light within a range of wavelengths is incident on an active portion of the photodetector 260. The photodetector 260 is responsive to light in the red and infrared portions of the electromagnetic spectrum. The amount of conductivity of the photodetector 260 is dependent on the intensity of the light incident on it. Thus, when the oximeter sensor 212 is mounted on a patient's finger, for example, as illustrated for the oximeter sensor 112 in FIG. 1A, the light from the light-emitting diodes 250, 252, which are typically mounted on one side of the finger (e.g., the upper side as shown in FIG. 1A), passes through the finger and impinges on the photodetector 260, which is mounted on the opposite side of the finger (e.g., the lower sides as shown in FIG. 1A). As described in the above-referenced patents, a signal responsive to the conductivity of the photodetector 260 is advantageously measured to determine the intensity of the light passing through the portion of the patient's body in response to the activation of the red light-emitting diode 250 and to determine the intensity of the light passing through the portion of the patient's body in response to the activation of the infrared light-emitting diode 252. Because the intensities detected in response to the two different wavelengths vary in response to blood oxygenation levels, the blood oxygenation level of the patient can be determined from the measured signals.

The signals caused by variations in the conductivity of the photodetector 260 in response to the light are provided as inputs to the receiving and conditioning subsystem 234, which receives the signals, conditions the signals, and provides the conditioned signals to the controller 230. The controller 230 further processes the conditioned signals to determine blood oxygenation levels and pulse rate, and generates signals to the display subsystem 236 to cause the blood oxygenation levels and pulse rate to be visibly displayed. In addition, audible signals (e.g., alarm signals) may be provided. The information may also be recorded by the oximeter monitor 210 or provided to other devices (not shown) via an input/output interface (not shown).

As, shown in FIG. 2, the first light-emitting diode 250 and the second light-emitting diode 252 are connected in a common-anode configuration. One skilled in the art will appreciate that the two light-emitting diodes 250, 252 can also be connected in a common-cathode configuration (not shown) with appropriate changes in the voltage reference. The cathode of the first light-emitting diode 250 is electrically connected via respective first contacts in the connector 224 and the connector 228, via a first wire 270 in the cable 220, via respective first contacts in the connector 226 and the connector 222, to the LED driver subsystem 232. The anode of the first light-emitting diode 250 is electrically connected via respective second contacts in the connector 224 and the connector 228, via a second wire 272 in the cable 220, via respective second contacts in the connector 226 and the connector 222, to the LED driver subsystem 232. The cathode of the second light-emitting diode 252 is electrically connected via respective third contacts in the connector 224 and the connector 228, via a third wire 274 in the cable 220, via respective third contacts in the connector 226 and the connector 222, to the LED driver subsystem 232. The anode of the second light-emitting diode 252 is connected in common with the anode of the first light-emitting diode 250, and is therefore also connected to the LED driver subsystem 232 via the respective second contacts and the second wire 272.

The anode of the photodetector 260 is connected via respective fourth contacts in the connector 224 and the connector 228, via a fourth wire 276 in the cable 220, via respective fourth contacts in the connector 226 and the connector 222, to the signal receiving and conditioning subsystem 234. The cathode of the photodetector 260 is electrically connected via respective fifth contacts in the connector 224 and the connector 228, via a fifth wire 278 in the cable 220, and via respective fifth contacts in the connector 226 and the connector 222, to the receiving and conditioning subsystem 234.

As discussed in more detail in the above-referenced patents, the first light-emitting diode 250 is activated to emit light by sinking a current from the cathode of the first light-emitting diode 250 by applying a relatively low voltage to the cathode with respect to the anode. In similar manner, the second light-emitting diode 252 is activated to emit light by sinking a current from the cathode of the second light-emitting diode 252 by applying a relatively low voltage to the cathode. As further discussed in the referenced patents, the low drive voltages are typically applied to the two cathodes of the light-emitting diodes in an alternating pattern so that only one light-emitting diode is active at any time. Furthermore, the alternating driving pattern is typically set so that a selected time duration is provided after each light-emitting diode is driven during which neither light-emitting diode is being driven.

The light emitted by each of the light-emitting diodes 250, 252 is detected by the photodetector 260, which generates a signal responsive to variations in the intensity of the detected light. The signal generated by the photodetector 260 is sensed by the receiving and conditioning subsystem via the two wires 276 and 278 and the contacts in the connectors, as described above. In order to reduce the effect of noise on the signals sensed via the two wires 276, 278, the two wires 276, 278 are preferably surrounded by a flexible shield (e.g., wire braid) 280, which, in the illustrated embodiment, is grounded within the oximeter monitor 210 via respective shielding contacts in the connectors 226, 222. (Note that references herein to four-wire and five-wire systems do not include the shielding and its associated connections in the number of wires.)

As further shown in phantom lines in FIG. 2, the oximeter sensor 212 may advantageously include a resistor 290 connected in parallel across one of the light-emitting diodes (e.g., the light-emitting diode 250 in FIG. 2). As described, for example, in U.S. Pat. No. 5,758,644, which is incorporated by reference herein, the resistor 290 is advantageously used to identify the sensor 212. In particular, when a voltage is applied across the resistor 290 that is less than the voltage required to activate the diode 250, a current flows through the resistor 290 that is determined by the resistance of the resistor 290. The current can be measured to determine the resistance of the resistor 290. The resistance of the resistor 290 can be used to identify the sensor 212. For example, sensors having different characteristics (e.g., pediatric, neonatal, adult, etc.) can be identified with different resistance values.

Figure 3:
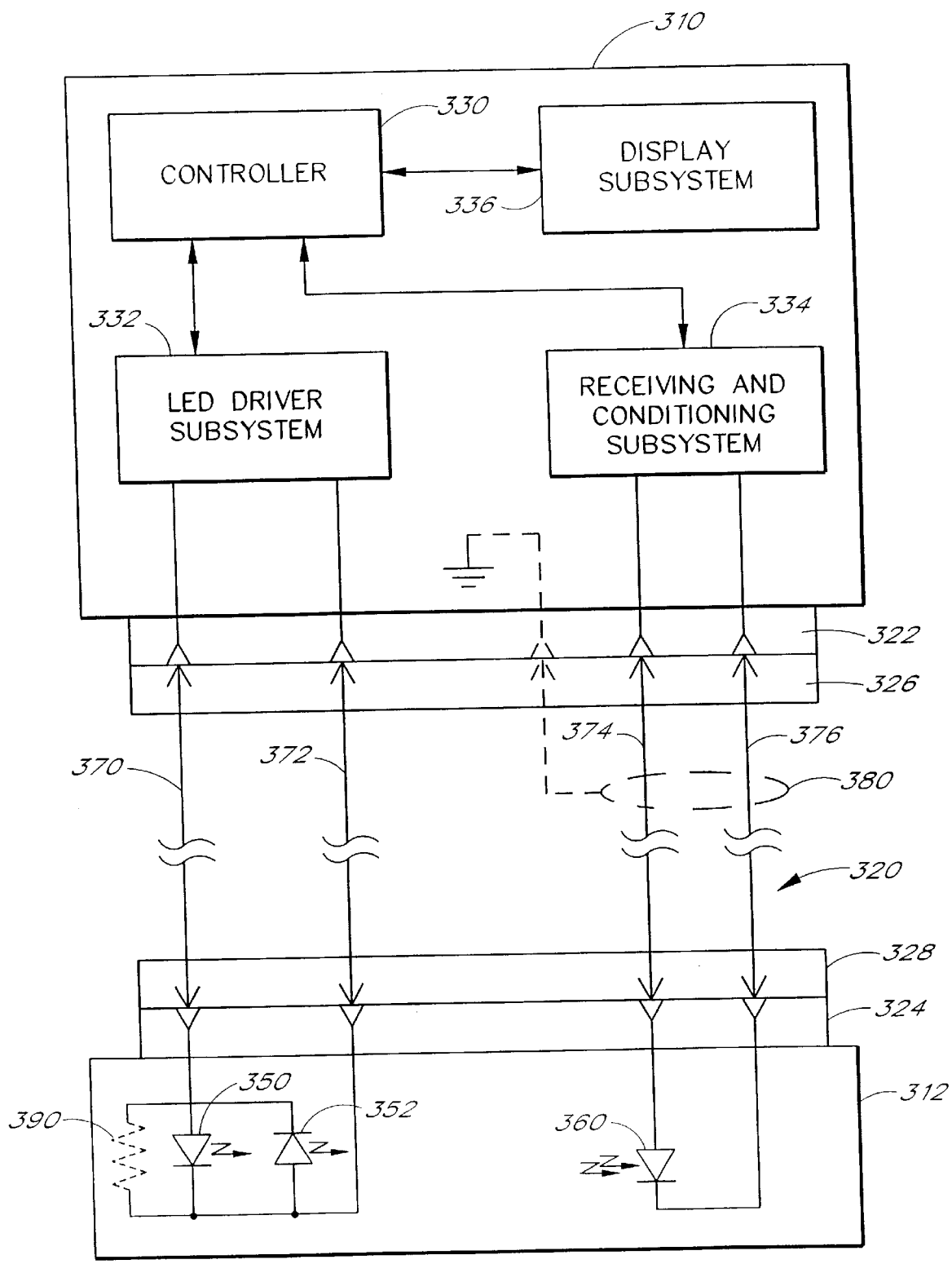
FIG. 3 illustrates a schematic block diagram of an oximeter system that implements the oximeter system of FIG. 1 with light-emitting diodes connected in back-to-back configuration (i.e., the anode of a first diode connected to the cathode of a second diode and the cathode of the first diode connected to the anode of the second diode)

FIG. 3 illustrates an oximeter system that incorporates a four-wire interconnection cable 320 between an oximeter monitor 310 and the oximeter sensor 312. The oximeter monitor 310 is similar to the oximeter monitor 210 in FIG. 2, and like elements have been numbered accordingly with each element number in FIG. 2 increased by 100 in FIG. 3.

Unlike the LED driver subsystem 232 in FIG. 2, the LED driver subsystem 332 in FIG. 3 only has two connections to the monitor connector 322. Also unlike the corresponding elements in FIG. 2, the first light-emitting diode 350 and the second light-emitting diode 352 in FIG. 3 do not have their respective anodes interconnected in common. Rather, in FIG. 3, the anode of the first light-emitting diode 350 is connected to the cathode of the second light-emitting diode 352. The cathode of the first light-emitting diode 350 is connected to the anode of the second light-emitting diode 352. The photodetector 360 in FIG. 3 is connected in a similar manner to the connection of the photodetector 260 in FIG. 2.

The commonly connected anode of the first light-emitting diode 350 and cathode of the second light-emitting diode 352 are connected via respective first contacts in the connectors 324 and 328, via a first wire 370 in the cable 320, and via respective first contacts in the connectors 326 and 322, to the LED driver subsystem 332.

The commonly connected cathode of the first light-emitting diode 350 and anode of the second light-emitting diode 352 are connected via respective second contacts in the connector 324 and the connector 328, via a second wire 372 in the cable 320, and via respective second contacts in the connector 326 and the connector 322, to the LED driver subsystem 332.

The anode of the photodetector 360 is connected via respective third contacts in the connector 324 and the connector 328, via a third wire 374 in the cable 320, via respective third contacts in the connector 326 and the connector 322, to the signal receiving and conditioning subsystem 334. The cathode of the photodetector 360 is connected via respective fourth contacts in the connector 324 and the connector 328, via a fourth wire 376 in the cable 320, via respective fourth contacts in the connector 326 and the connector 322, to the signal receiving and conditioning subsystem 334.

Unlike the sensor 212 of FIG. 2, the sensor 312 of FIG. 3 does not drive each light-emitting diode 350, 352 with a separate signal via a unique signal wire. Rather, in FIG. 3, both light-emitting diodes 350, 352 are connected to the same pair of signal wires. Thus, in FIG. 3, the first light-emitting diode 350 is activated by applying a relatively positive voltage to the common connection of the anode of the first light-emitting diode 350 and the cathode of the second light-emitting diode 352. The relatively positive voltage is applied with respect to the common connection of the cathode of the first light-emitting diode 350 and the anode of the second light-emitting diode 352. Thus, the first light-emitting diode 350 is forward biased from the anode to the cathode, and the second light-emitting diode 352 is reverse-biased from the cathode to the anode. Therefore, only the first light-emitting diode 350 is activated.

In similar manner, the second light-emitting diode 352 is activated by applying a relatively positive voltage to the common connection of the anode of the second light-emitting diode 352 and the cathode of the first light-emitting diode 352. The relatively positive voltage is applied with respect to the common connection of the cathode of the second light-emitting diode 352 and the anode of the first light-emitting diode 350. Thus, the second light-emitting diode 352 is forward biased from the anode to the cathode, and the first light-emitting diode 350 is reverse-biased from the cathode to the anode. Therefore, only the second light-emitting diode 352 is activated.

As further illustrated in FIG. 3, the oximeter sensor 312 may advantageously include an optional resistor 390 (shown in phantom) connected in parallel across the light-emitting diodes 350, 352. As discussed above in connection with the resistor 290 in FIG. 2, the resistor 390 is advantageously used to identify the sensor 312 when a voltage is applied across the resistor 390 that is less than the voltage required to activate either the light-emitting diode 350 or the light-emitting diode 352.

It can be seen from FIGS. 2 and 3 and from the foregoing description that the sensor 212 requires five sets of signal conductors (i.e., contacts and signal wires) to provide the three drive signals and the two sensing signals. In contrast, the sensor 312 requires only four sets of conductors to provide the dual-polarity drive signal and the two sensing signals. Thus, without the conventional bulky conversion systems discussed in the background, the sensor 212 cannot be used in an oximeter system designed for the sensor 312, and the sensor 312 cannot be used in an oximeter system designed for the sensor 212. Thus, typically a hospital having both types of oximeter systems stocks both types of sensors 212, 312.

Figure 4A:
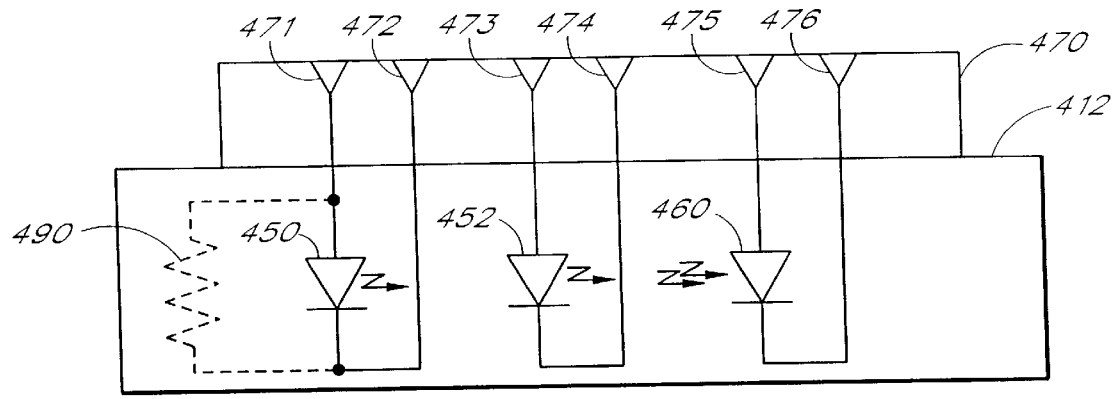
FIG. 4A illustrates an embodiment of an oximeter sensor in accordance with the present invention that operates with the oximeter monitor of FIG. 2 or with the oximeter monitor of FIG. 3.

As illustrated in FIG. 4A, one embodiment of the present invention is an oximeter sensor 412 that operates with either a five-wire oximeter system or a four-wire oximeter system. The improved oximeter sensor 412 includes a first (e.g., red) light-emitting diode 450 and a second (infrared) light-emitting diode 452. Each light-emitting diode 450, 452 has a respective anode and a respective cathode. The sensor 412 further includes a photodetector 460, which has a first terminal and a second terminal and which operates as discussed above. Unlike the known devices discussed above, the anode and the cathode of each light-emitting diode 450, 452 are coupled to separate connector pins (i.e., contacts) in a connector 470 of the sensor 412. In particular, the anode of the first light-emitting diode 450 is coupled to a first connector pin 471, and the cathode of the first light-emitting diode 450 is coupled to a second connector pin 472. The anode of the second light-emitting diode 452 is coupled to a third connector pin 473, and the cathode of the second light-emitting diode 452 is coupled to a fourth connector pin 474. The anode of the photodetector 460 is coupled to a fifth connector pin 475, and the cathode of the photodetector 460 is coupled to a sixth connector pin 476. The sensor 412 may advantageously include a resistor 490 connected across one of the light-emitting diodes (e.g., the first light-emitting diode 450). Alternatively, the resistor 490 may be coupled to independent connector pins as discussed below in connection with FIG. 4B.

The six connector pins 471–476 of the sensor 412 are not directly connectable to either the five-wire oximeter system 210 of FIG. 2 or the four-wire oximeter system 310 of FIG. 3. Thus, the sensor 412 is used in combination with a first interconnector 500 (shown in FIG. 5A) to interconnect the sensor 412 with a five-wire oximeter system 210 and a second interconnector 600 (shown in FIG. 6A) to interconnect the sensor 412 with a four-wire oximeter system 310. The interconnectors 500, 600 may be solid interconnectors having first and second connectors in a common shell, as illustrated by the interconnector 500 in FIG. 5A. In the alternative, the interconnectors 500, 600 may be constructed as cables having a connector at each end, as illustrated by the interconnector 600 in FIG. 6A.

Figure 4B:
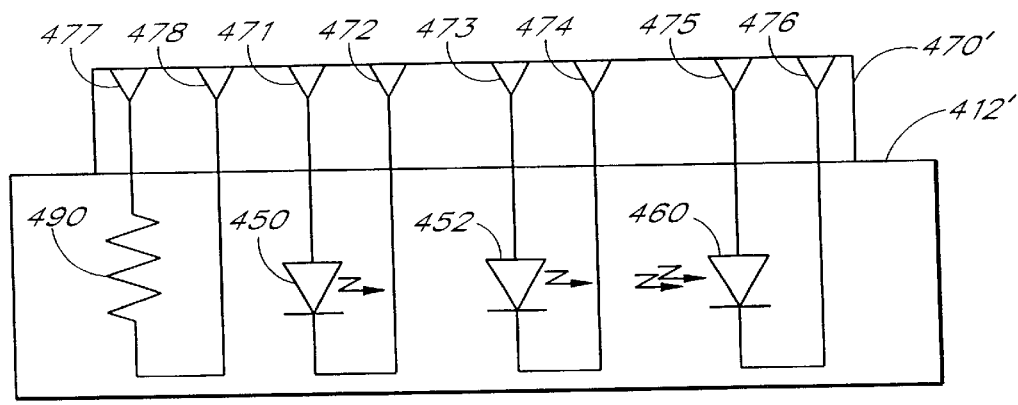
FIG. 4B illustrates an alternative embodiment of the oximeter sensor of FIG. 4A with additional connections for a resistor.

FIG. 4B illustrates an alternative sensor 412' in accordance with the present invention. The sensor 412' is similar to the sensor 412 of FIG. 4A except that the resistor 490 is not connected across the first light-emitting diode 450. Rather, in the sensor 412', the first terminal of the resistor 490 is connected to a seventh contact 477 in a connector 470', and the second terminal of the resistor 490 is connected to an eighth contact 478 in the connector 470'. The alternative sensor 412' will be further discussed below in connection with FIGS. 5B and 6B.

Figure 5A:
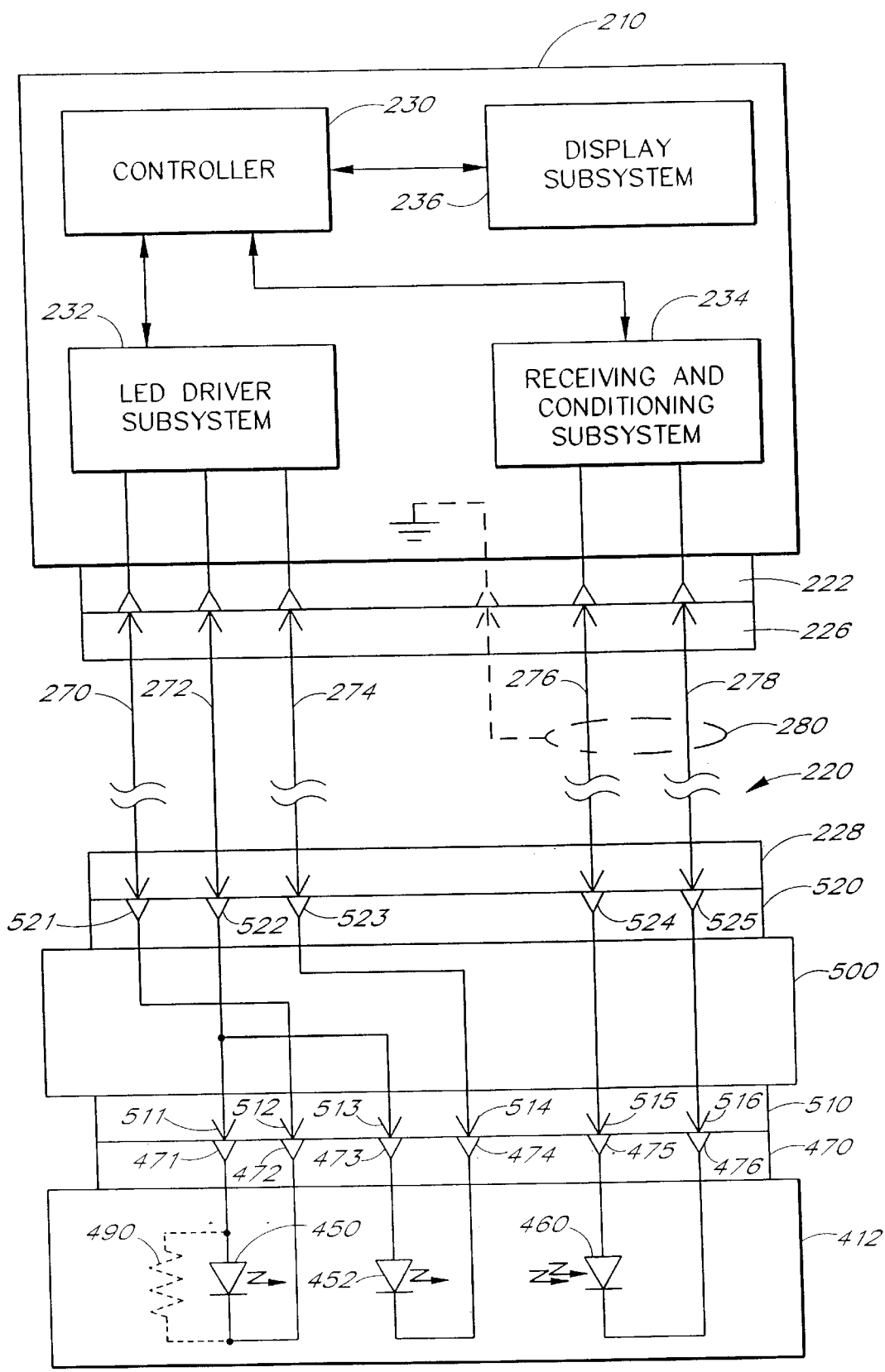
FIG. 5A illustrates the oximeter sensor of FIG. 4A in combination with an interconnector that interconnects the oximeter sensor with the oximeter monitor of FIG. 2 so that the oximeter sensor is interconnected with the light-emitting diodes in a common anode configuration.

As illustrated in FIG. 5A, the interconnector 500 has a first connector 510 at a first end. The connector 510 has six contacts 511–516 for engaging the connector pins 471–476 of the sensor 412. The interconnector 500 has a second connector 520 at a second end. The connector 520 has five contacts 521–525 for engaging the first, second, third, fourth and fifth contacts, respectively, in the connector 228 of the five-wire cable 220 that connects to the five-wire oximeter system 210 of FIG. 2. As illustrated, the contact 512 is connected to the contact 521, which is connected to the first wire 270 in the cable 220, and thus electrically connects the cathode of the first (red) light-emitting diode 450 to the red driver output of the LED driver subsystem 232. The contact 514 is connected to the contact 523, which is connected to the third wire 274 in the cable 220, and thus electrically connects the cathode of the second (infrared) light-emitting diode 452 to the infrared driver output of the LED driver subsystem 232. The contacts 511 and 513 are electrically interconnected within the interconnector 500 and are electrically connected to the second contact 512 of the connector 510, which is connected to the second wire 272 in the cable 220. Thus, the anodes of both light-emitting diodes 450, 452 are electrically connected to the LED driver subsystem 232 in the oximeter monitor 210.

The contact 515 is connected to the contact 524, which is connected to the fourth wire 276 in the cable 220, and thus electrically connects the anode of the photodetector 460 to the receiving and conditioning subsystem 234. The contact 516 is electrically connected to the fifth contact 525, which is connected to the fifth wire 278 in the cable 220. Thus, the cathode of the photodetector 460 is connected to the receiving and conditioning subsystem 234. Note that the shield 280 around the fourth wire 276 and the fifth wire 278 is part of the cable 220, as discussed above in connection with FIG. 2.

Figure 5B:
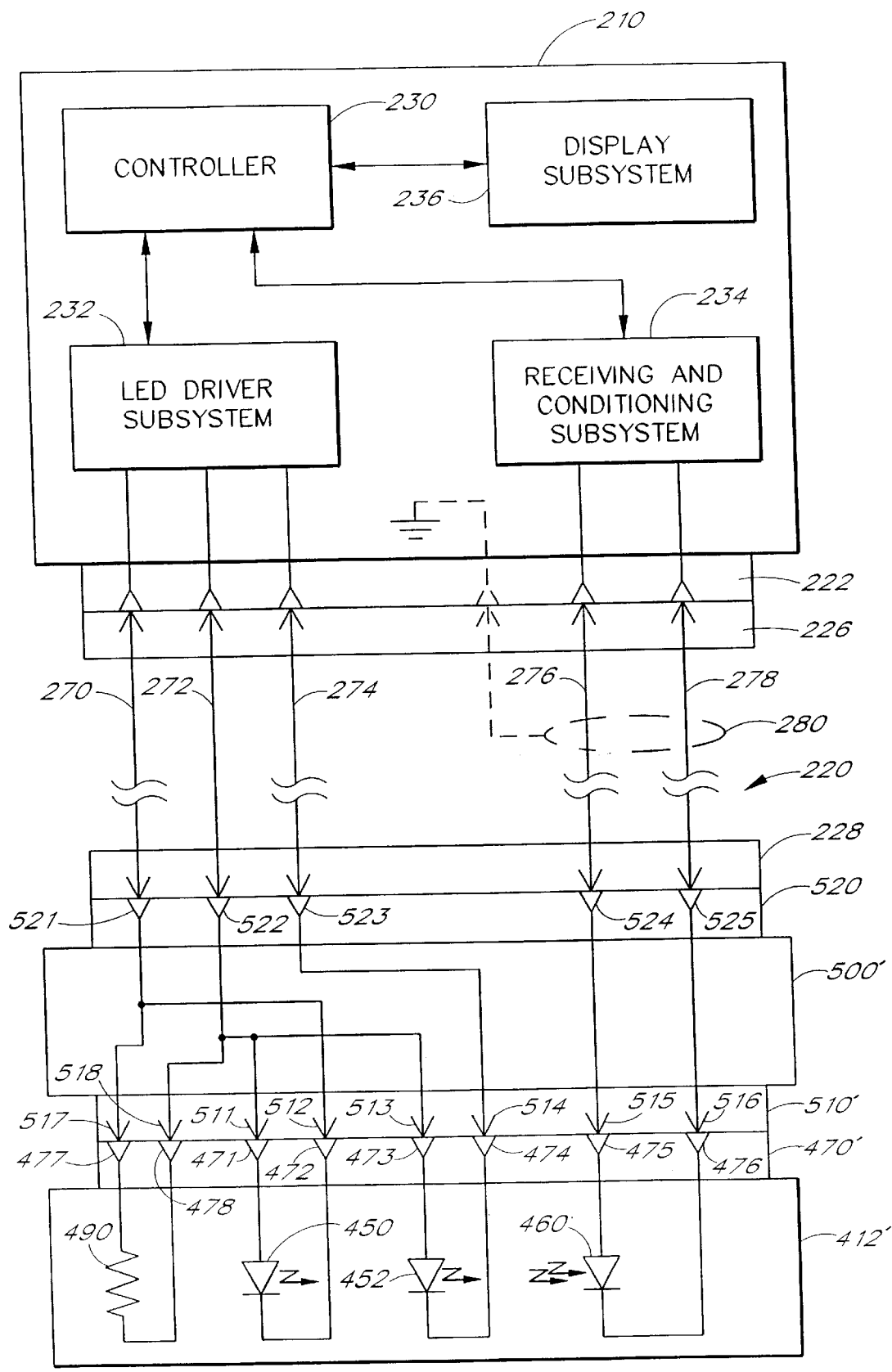
FIG. 5B illustrates the oximeter sensor of FIG. 4B in combination with an interconnector that interconnects the oximeter sensor with the oximeter monitor of FIG. 2 so that the oximeter sensor is interconnected with the light-emitting diodes in a common anode configuration.

FIG. 5B illustrates an interconnector 500' that is used in combination with the alternative sensor 412' of FIG. 4B to interconnect the alternative sensor 412' with the five-wire oximeter system 210. As described above, the resistor 490 in the sensor 412' has two independent contacts 477 and 478 in the connector 470'. A connector 510' in the alternative interconnector 500' is similar to the connector 510 of the interconnector 500; however, the connector 510' includes two additional contacts 517 and 518 that engage the resistor contacts 477, 478. In FIG. 5B, the contacts 517, 518 are electrically connected to the signal lines that are connected to the anode and the cathode, respectively, of the first light-emitting diode 450 so that the resistor 490 is effectively connected across the first light-emitting diode 450. Thus, the interconnector 500' connects the resistor 490 to provide the same electrical impedance characteristic as the sensor 212 of FIG. 2. It should be understood that the interconnector 500' can be modified to connect the resistor 490 across the second light-emitting diode 452 or across the photodetector 460. As a further alternative, the contacts 517, 518 do not have to be connected, in which case the resistor 490 is not connected to the oximeter circuitry. Thus, the alternative sensor 412' and interconnector 500' provide additional flexibility in providing compatibility with other sensor configurations.

Figure 6A:
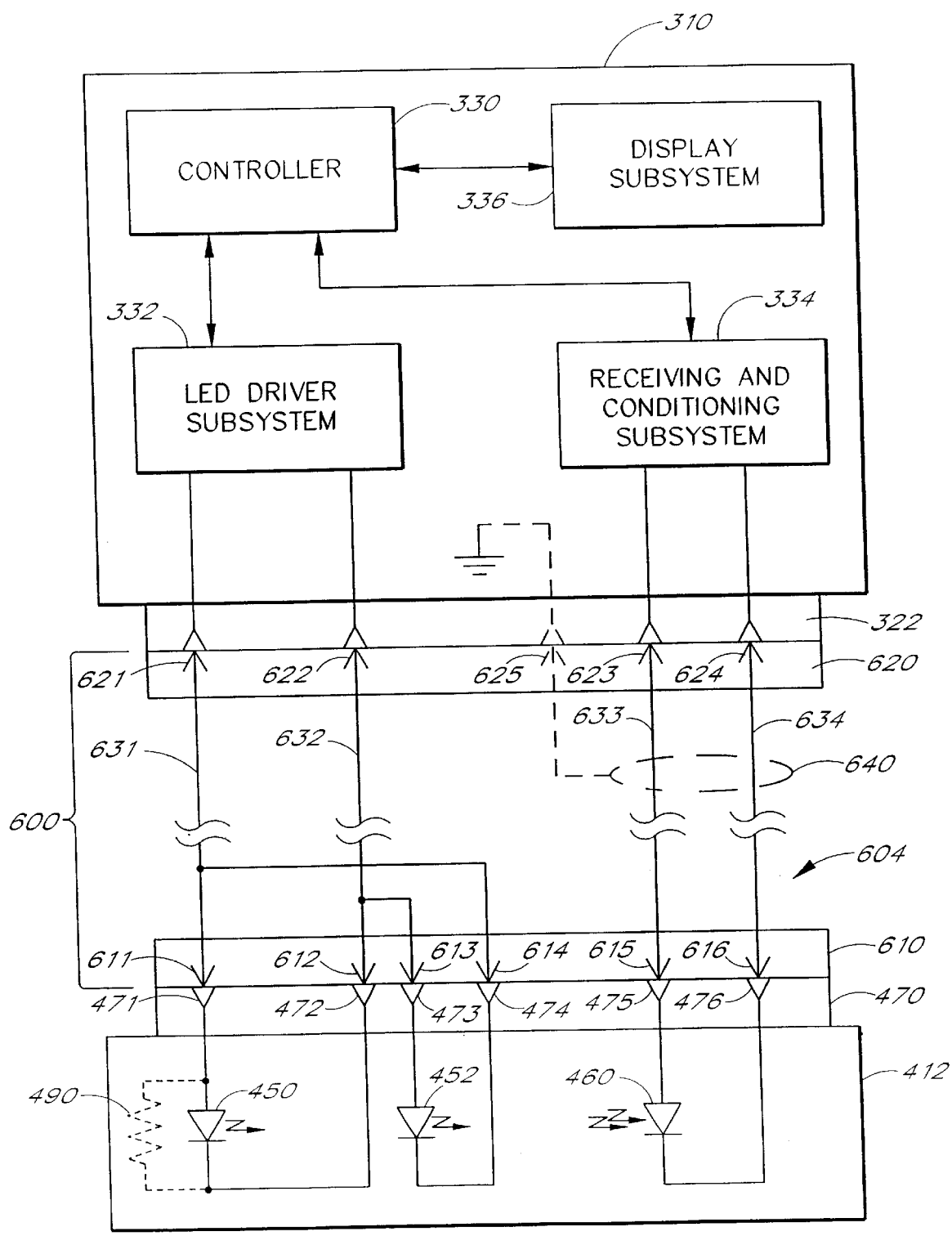
FIG. 6A illustrates the oximeter sensor of FIG. 4A in combination with an interconnection cable that interconnects the oximeter sensor with the oximeter monitor of FIG. 3 so that the oximeter monitor is interconnected with the light-emitting diodes in the a back-to-back configuration.

The interconnector 600 in FIG. 6A comprises a flexible cable 604 having a first connector 610 having six contacts 611–616 for engaging the connector pins 471–476 in the connector 470 of the sensor 412. The flexible cable 604 of the interconnector 600 has a second connector 620 having five contacts 621–625. The second connector 620 engages the connector 322 of the four-wire oximeter system 310.

The contacts 611 and 614 in the connector 610 are electrically connected together in the cable 604 and are connected to the contact 621 in the connector 620 via a first wire 631 in the cable 604. Thus, the anode of the first light-emitting diode 450 and the cathode of the second light-emitting diode 452 are connected together in common, and the common connection is connected to the LED driver subsystem 332 in the oximeter monitor 310.

The contacts 612 and 613 of the connector 610 are electrically connected together in the cable 604 and are connected to the contact 622 of the connector 620 via a second wire 632 in the cable 604. Thus, the cathode of the first light-emitting diode 450 and the anode of the second light-emitting diode 452 are connected together and are connected to the LED driver subsystem 334 in the oximeter monitor 310.

The contact 615 of the connector 610 is electrically connected to the contact 623 in the connector 620 via a third wire 633 in the cable 604. Thus, the anode of the photodetector 460 is connected to the receiving and conditioning subsystem 334 in the oximeter monitor 310. The contact 616 of the connector 610 is electrically connected to the contact 624 in the connector 620 via a fourth wire 634 in the cable 604. Thus, the cathode of the photodetector 460 is connected to the receiving and conditioning subsystem 334 in the oximeter monitor 310. The third wire 633 and the fourth wire 634 are preferably surrounded by a flexible shield 640, which is connected to the fifth contact 625 in the connector 620, and thus to a ground connection in the oximeter monitor 310.

Figure 6B:
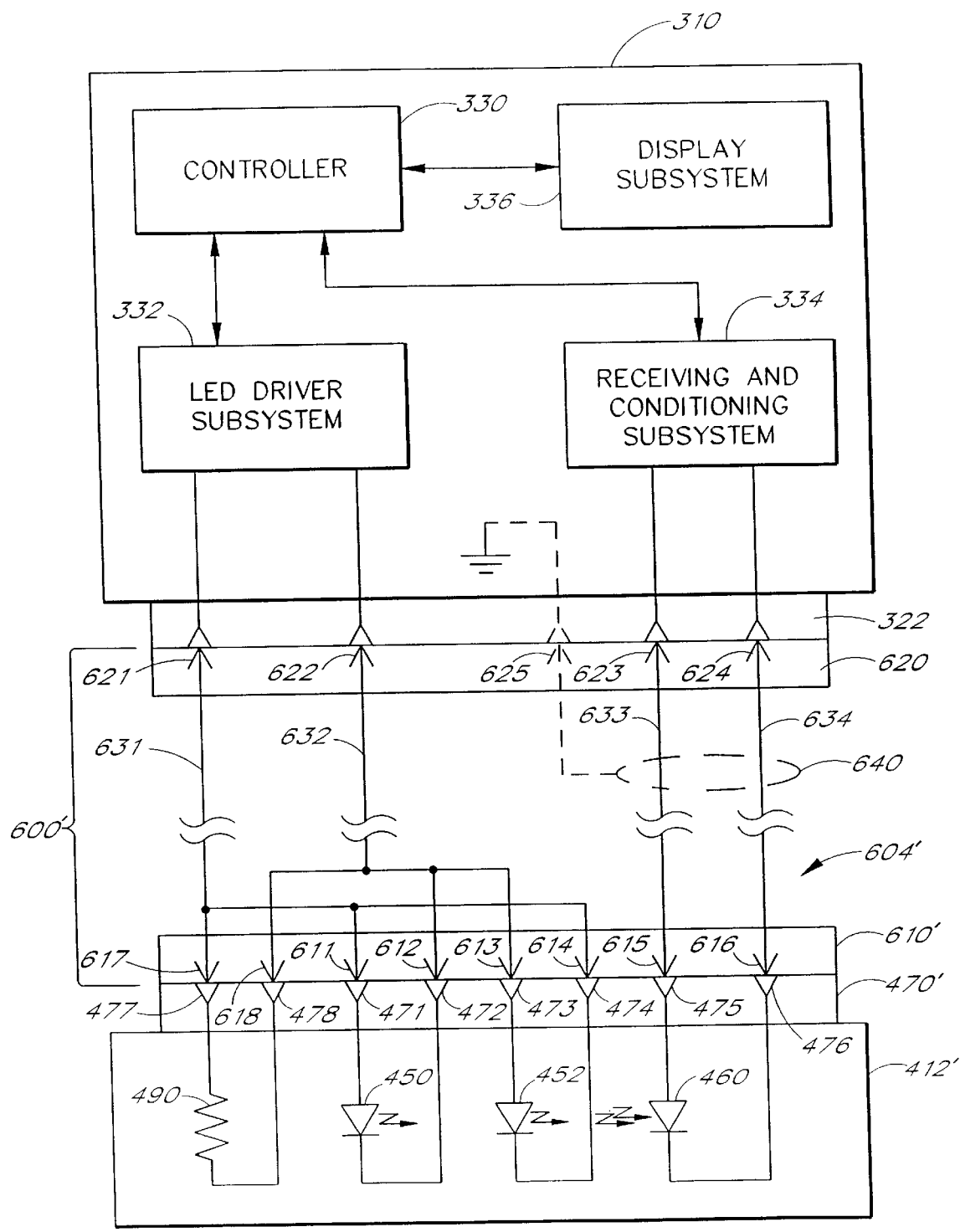
FIG. 6B illustrates the oximeter sensor of FIG. 4B in combination with an interconnection cable that interconnects the oximeter sensor with the oximeter monitor of FIG. 3 so that the oximeter monitor is interconnected with the light-emitting diodes in a back-to-back configuration.

FIG. 6B illustrates an alternative cable interconnector 600' for use with the alternative sensor 412' of FIG. 4B. The cable interconnector 600' is similar to the cable interconnector 600 of FIG. 6A except that a connector 610' includes a seventh contact 617 and an eighth contact 618 to engage the seventh contact 477 and the eighth contact 478 of the connector 470' of the sensor 412'. In addition, a cable 604' advantageously includes electrical interconnections from the seventh contact 617 and the eighth contact 618 to selected signal lines in the cable 604'. For example, in FIG. 6B, the seventh contact 617 is electrically connected to the first signal line 631 and the eighth contact 618 is electrically connected to the second signal line 632 so that the resistor 490 is electrically connected across the two back-to-back diodes 450, 452. It should be understood that the interconnector 600' can be modified to connect the resistor 490 across the photodetector 460. As a further alternative, the contacts 617, 618 do not have to be connected in the cable 604', in which case the resistor 490 is not connected to the oximeter circuitry. Thus, the alternative sensor 412' and interconnector 600' provide additional flexibility in providing compatibility with other sensor configurations.

It should be noted that the interconnector embodiments 500, 500' of FIGS. 5A and 5B are particularly advantageous if the cable 220 is not intended to be a disposable item and is sold with the monitor 210. Thus, the interconnectors 500, 500' permit the existing monitor 210 and cable 220 to continue to be used together. The interconnectors 500, 500' can be produced as disposable items or as a non-disposable items.

The cable interconnector embodiments 600 and 600' of FIGS. 6A and 6B are particularly advantageous if the original cable 320 was intended to be a disposable item. In such a case, the cable interconnectors 600, 600' can likewise be disposable and there is no need to manufacture the extra connectors required to produce the interconnectors 500, 500' of FIGS. 5A and 5B.

It should be understood that the interconnectors 500, 500', 600, 600' are not limited to use with the sensor and monitor configurations shown above. For example, the interconnectors can be configured to connect the light-emitting diodes 450, 452 in a common cathode configuration. Thus, the present invention provides flexibility as well as compatibility with existing oximeter monitors.

The pulse oximeter sensor has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A physiological monitoring system comprising:

a sensor including first sensor elements capable of irradiating a measurement site with light of at least one wavelength and one or more second sensor elements capable of detecting the light after transmission through tissue of the measurement site, wherein the first sensor elements are capable of being passively electrically connected in two or more configurations using all of the first sensor elements;

a sensor connector including a first number of sensor contacts connected to conductive material capable of providing electrical communication to at least the first sensor elements and a second number of sensor contacts connected to conductive material capable of providing electrical communication to at least the second sensor elements;

a monitoring device capable of determining at least one physiological parameter of a patient from one or more signals communicated from the second sensor elements;

a monitor connector including a first number of monitor contacts connected to conductive material capable of communicating signals to or from the monitoring device for the first sensor elements and including a second number of monitor contacts connected to conductive material capable of communicating signals to or from the monitoring device for the second sensor elements, wherein the first number of monitor contacts is different from the first number of sensor contacts;

a cable compatible with the monitor connector and incompatible with the sensor connector, the cable including a first cable connector attached to one end of the cable and adapted to connect to the monitor connector, and a second cable connector attached to the other end of the cable;

a first adapter which is capable of passively electrically connecting the sensor connector to the second cable connector to configure the sensor in one of the two or more configurations, thereby establishing electrical communication between the first number of monitor contacts to the first number of sensor contacts; and a second adapter which is capable of passively electrically connecting the sensor connector to the second cable connector to configure the sensor in another of the two or more configurations, thereby establishing electrical communication between the first number of monitor contacts to the first number of sensor contacts.

2. The physiological monitoring system of claim 1, wherein the first number of sensor contacts comprises two terminals for each of the first sensor elements.

3. The physiological monitoring system of claim 1, wherein the second number of sensor contacts comprises two terminals for each of the second sensor elements.

4. The physiological monitoring system of claim 1, wherein at least some of the first number of sensor contacts correspond to conductive material communicating with an information element.

5. The physiological monitoring system of claim 4, wherein the information element is electrically parallel to at least one of the first sensor elements.

6. The physiological monitoring system of claim 1, wherein the adapter passively electrically configures the first sensor elements in a common cathode configuration.

7. The physiological monitoring system of claim 1, wherein the adapter passively electrically configures the first sensor elements in a common anode configuration.

8. The physiological monitoring system of claim 1, wherein the adapter passively electrically configures the first sensor elements in a back-to-back configuration where an anode of one of the first sensor elements electrically communicates with the cathode of another of the first sensor elements.

9. A method of connecting a sensor having a sensor connector of a first type to a physiological monitoring device having a monitor connector of a second type, wherein the first type is different from the second type, the method comprising:

passively connecting through an adapter other than a dedicated cable, a first number of cable contacts in a cable connection assembly for a cable communicating with a physiological monitoring device, and a first number of sensor contacts in a sensor connection assembly for a sensor capable of multiple configurations using only the same sensor elements for each configuration, wherein the first number of cable contacts do not equal the first number of sensor contacts and wherein the first number of cable contacts supply at least one drive signal to the sensor; and passively connecting through the adapter, a second number of cable contacts in the cable connection assembly, to a second number of sensor contacts in the sensor connection assembly, wherein the second number of cable contacts and the second number of sensor contacts provide at least one detector signal to the physiological monitoring device.

10. The method of claim 9, wherein the passively connecting of the first number of cable contacts configures a sensor in a common cathode configuration.

11. The method of claim 9, wherein the passively connecting of the first number of cable contacts configures a sensor in a common anode configuration.

12. The method of claim 9, wherein the passively connecting of the first number of cable contacts configures a sensor in a back-to-back configuration.

* * * * *

UNITED STATES PATENT AND TRADEMARK OFFICE
CERTIFICATE OF CORRECTION

PATENT NO.    : 6,697,656 B1
DATED         : February 24, 2004
INVENTOR(S)   : Al-Ali, Ammar It is certified that error appears in the above-identified patent and that said Letters Patent is hereby corrected as shown below:

Title page,
Item [74], *Attoreny, Agent, or Firm*, after "Martens" please insert -- , --; and after "Bear" please insert -- , --.

Column 5,
Line 47, after "As" please delete ",".

Column 12,
Lines 20, 23 and 26, after "wherein the" please insert -- first --.
Line 37, after "connecting through" please delete "an" and insert -- one of a first --.
Lines 37-38, after "adapter" please delete "other than a dedicated cable," and insert -- or a second adapter, --.
Line 46, before "the first number" please delete "wherein".
Line 47, after "to the sensor" please insert -- , and wherein the first adapter configures the sensor in one of the multiple configurations and the second adapter configures the sensor in another of the multiple configurations --.
Line 48, after "through the" please insert -- one of the first --.
Line 48, after "adapter" please insert -- or the second adapter --.

Signed and Sealed this

Twenty-fifth Day of October, 2005

JON W. DUDAS
*Director of the United States Patent and Trademark Office*